United States Patent [19]

Buckle et al.

[11] 3,974,289

[45] Aug. 10, 1976

[54] COUMARIN DERIVATIVES FOR THE TREATMENT OF ALLERGIES

[75] Inventors: Derek Richard Buckle, Redhill; Harry Smith, Maplehurst, near Horsham; Barrie Christian Charles Cantello, Horsham, all of England

[73] Assignee: Beecham Group Limited, England

[22] Filed: Apr. 15, 1974

[21] Appl. No.: 461,267

[30] Foreign Application Priority Data

Apr. 19, 1973 Germany.............................. 18876

[52] U.S. Cl. ........................... 424/281; 260/295 F; 260/343.2 R; 424/263; 424/283
[51] Int. Cl.² ......................................... A61K 31/37
[58] Field of Search.................... 424/283, 281, 263

[56] References Cited

UNITED STATES PATENTS

| 3,484,445 | 12/1969 | Lee et al............................. 424/283 |
| 3,567,832 | 3/1971 | Boschetti et al..................... 424/281 |
| 3,652,765 | 3/1972 | Ellis et al............................ 424/283 |
| 3,864,493 | 2/1975 | Cairns et al......................... 424/283 |
| 3,879,544 | 4/1975 | Reisner et al....................... 424/337 |
| 3,883,653 | 5/1975 | Barth................................. 424/251 |
| 3,885,038 | 5/1975 | Pfister et al........................ 424/283 |

Primary Examiner—Norman A. Drezin

[57] ABSTRACT

Pharmaceutical compositions for the treatment of allergies are produced using coumarin derivatives as the active agent. Certain of these compounds and their salts are novel.

58 Claims, No Drawings

COUMARIN DERIVATIVES FOR THE TREATMENT OF ALLERGIES

This invention relates to pharmaceutical compositions which are useful in the inhibition of the effects of certain types of antigen-antibody reactions, and are therefore of value in the prophylaxis and treatment of diseases associated with allergic or immunological reactions, e.g. certain types of asthma and hay-fever and also in the treatment of rhinitis. The invention also includes a number of new 3-nitrocoumarins and a method for their preparation.

We have discovered that certain 3-nitrocoumarins have useful activity in mammals in that they inhibit the effects of certain types of anitgen-antibody reactions. In particular, they appear to inhibit the release of mediator substances, such as histamine, which are normally released after antigen-antibody combinations and which appear to mediate the allergic response. The class of 3-nitrocoumarins which we have found to be active in this way has formula (I):

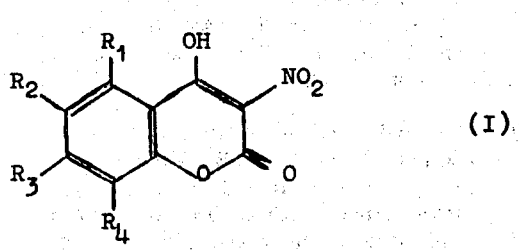

and the salts of compound (I) are also active. In formula (I) $R_1$, $R_2$, $R_3$ and $R_4$ are each hydrogen or alkyl, alkoxy, aryloxy, aralkoxy, aryl, aralkyl, heterocyclic, hydroxy, nitro, or halogen groups or any two of the groups $R_1$, $R_2$, $R_3$ and $R_4$ taken together with the carbon atoms to which they are attached complete a substituted or unsubstituted carbocyclic or heterocyclic ring system. However, a search of the chemical literature has revealed that not all the members of class (I) are novel compounds.

Below we list the compounds of formula (I) which we have found mentioned in the literature, together with the appropriate literature reference:

4-hydroxy-3-nitrocoumarin [3, 5, 6, 8, 10]
4-hydroxy-6-methyl-3-nitrocoumarin [1,2]
6,8-dimethyl-4-hydroxy-3-nitrocoumarin [9]
4-hydroxy-7-isopropyl-5-methyl-3-nitrocoumarin [5]
4-hydroxy-8-isopropyl-5-methyl-3-nitrocoumarin [5]
6-chloro-4-hydroxy-3-nitrocoumarin [11]
7-chloro-4-hydroxy-3-nitrocoumarin [2]
7-bromo-4-hydroxy-3-nitrocoumarin [2]
4,7-dihydroxy-3-nitrocoumarin [2,7]
4,7-dihydroxy-3,6-dinitrocoumarin [7]
4,7-dihydroxy-3,8-dinitrocoumarin [7]
4,7-dihydroxy-3,6,8-trinitrocoumarin [7]
4-hydroxy-5-methoxy-3-nitrocoumarin [2]
4-hydroxy-6-methoxy-3-nitrocoumarin [4]
4-hydroxy-7-methoxy-3-nitrocoumarin [2,4]
4-hydroxy-7-methoxy-8-methyl-3-nitrocoumarin [4]
3,6-dinitro-4-hydroxycoumarin [3]
7-acetamido-4-hydroxy-3-nitrocoumarin [2, 4, 12]

References

1. J. Chem. Soc.C. (1971), 218
2. Proc. Ind.Acad. Sci.Sect A. (1968), 67, 42
3. J.Amer. Chem.Soc., (1945), 67, 99
4. Yakugaku Zassi (1966), 86, 1064 (Chemical Abstracts 1967, 66,104869u)
5. Annalen (1961), 643, 97
6. Pharmazie (1953), 8, 221 (C.A. 48, 7602g.)
7. Chem. Pharm. Bull., (1971), 19, 1046
8. Monatsh (1958), 89, 787
9. Monatsh (1958), 89, 143
10. Arch. Pharm (1963), 296, 365
11. Glas. Hem. Tehndl. Bosne. Hercegovine (1968), 16, 109 (Chemical Abstracts 72, 43345V)
12. Chemical Abstracts 67, P 43681y Although the above compounds have been reported in the literature, no form of useful biological activity has been ascribed to them. Likewise there has been in the literature, no suggestion that such compounds are likely to possess any form of useful biological activity and in particular the discovery that they have anti-allergic activity has not been predicted in any way.

Accordingly, in its broadest aspect, the present invention provides a pharmaceutical composition having anti-allergy activity comprising a compound of formula (I) or a pharmaceutically acceptable salt thereof:

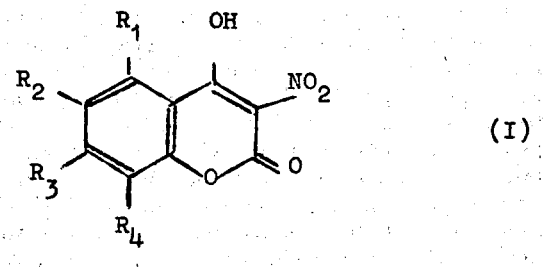

together with one or more pharmaceutically acceptable carriers, in which formula $R_1$, $R_2$, $R_3$ and $R_4$ represent hydrogen or alkyl, alkoxy, aryloxy, aralkoxy, aryl, aralkyl, heterocyclic, hydroxy, nitro, or halogen groups and any two of the groups $R_1$, $R_2$, $R_3$ and $R_4$ taken together with the carbon atoms to which they are joined complete a substituted or unsubstituted carbocyclic ring, said composition being adapted for administration to human beings.

Examples of groups $R_1$, $R_2$, $R_3$ and $R_4$ which may be present in compounds (I) are hydrogen, methyl, ethyl, n -and iso-propyl, n-, sec- and tert - butyl, methoxy, ethoxy, n-, and iso-propoxy, n-, sec- and tert - butoxy, phenoxy, benzyloxy, phenyl, benzyl, pyridyl, fluoro, chloro, bromo, iodo. In addition $R_1$ and $R_2$ and $R_3$ or $R_3$ and $R_4$ taken together with the carbon atoms to which they are attached may form a fused phenyl or fused 1,2-cyclohexenylene ring which may carry one or more of the substituents listed above.

Preferably $R_1$ and $R_4$ are hydrogen and $R_2$ and $R_3$ are each methyl, ethyl, n-propyl, methoxy, ethoxy or n-propoxy groups.

Examples of suitable salts of compounds of formula (I) include the alkali metal salts, particularly potassium and sodium, and the alkaline earth metal salts such as aluminium and magnesium salts, as well as salts with organic bases such as amines or amino compounds.

4-hydroxy-3-nitrocoumarins may exist in a number of tautomeric forms:

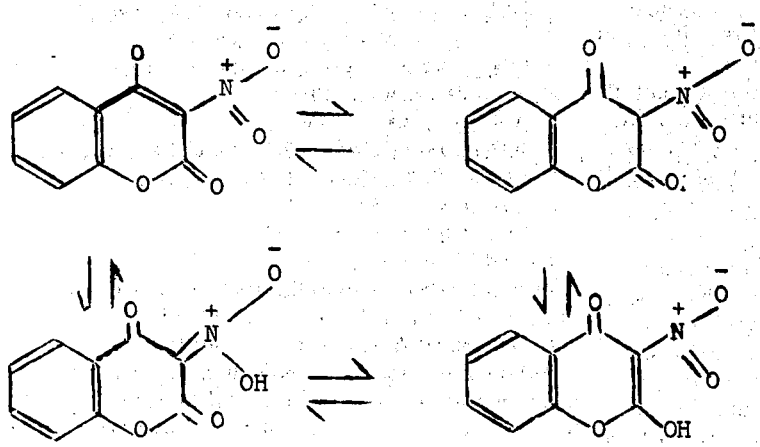

and it is to be understood that wherever in this specification we refer to 4-hydroxy-3-nitrocoumarins we also intend to include tautomeric forms of these compounds.

The compositions of this invention may be presented as a microfine powder for insufflation, e.g. as a snuff or in capsules of hard gelatin. They may also be presented with a sterile liquid carrier for injection. Compounds of formula (I) which are active when given by the oral route, may be compounded in the form of syrups, tablets, capsules, pills and the like. Preferably the compositions are in unit dosage form, or in a form in which the patient can administer to himself a single dosage. For example when the composition is in the form of a tablet, pill or capsule, a suitable dosage unit might contain from 1 to 500 mg of active ingredient. If desired, a small amount of bronchodilator compound such as isoprenaline may be incorporated into the compositions of this invention both to inhibit the cough response if the composition is insufflated and to provide immediate relief during an asthmatic attack. The effective dose of compound (I) depends on the particular compound employed, but is in general in the range of from 0.1 mg/kg/day to 100 mg/kg/day.

The precise nature of the pharmaceutical carrier used in the compositions of this invention is not important. Standard pharmaceutical practice may be followed.

As is common practice, the compositions will usually be accompanied by written or printed directions for use in the medical treatment concerned, in this case as an anti-allergic agent for prophylaxis treatment of, for example, asthma, hay-fever or rhinitis.

The present invention includes within its scope a preferred class of novel substituted 4-hydroxy-3-nitrocoumarins of formula (IA) and pharmaceutically acceptable salts thereof:

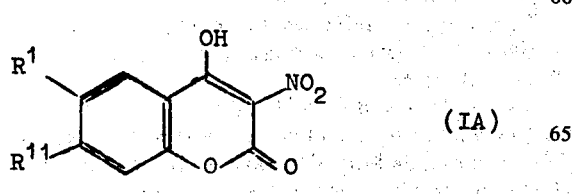

(IA)

wherein $R^1$ is hydrogen or methyl ethyl, n-propyl, methoxy, ethoxy or n-propoxy and $R^{11}$ is methyl, ethyl, n-propyl, methoxy, ethoxy or n-propoxy.

Compounds of formula (IA) which are particularly preferred include the following, and their pharmaceutically acceptable salts:

6,7-Dimethyl-4-hydroxy-3-nitrocoumarin
6,7-Diethyl-4-hydroxy-3-nitrocoumarin
6,7-Di-n-propyl-4-hydroxy-3-nitrocoumarin
6-Methyl-7-ethyl-4-hydroxy-3-nitrocoumarin
6-Ethyl-7-Methyl-4-hydroxy-3-nitrocoumarin
7-Methoxy-4-hydroxy-3-nitrocoumarin
7-Ethoxy-4-hydroxy-3-nitrocoumarin
7-n-Propoxy-4-hydroxy-3-nitrocoumarin
6-Methyl-7-methoxy-4-hydroxy-3-nitrocoumarin
6-Ethyl-7-methoxy-4-hydroxy-3-nitrocoumarin
6-n-Propyl-7-methoxy-4-hydroxy-3-nitrocoumarin
6-Methyl-7-ethoxy-4-hydroxy-3-nitrocoumarin
6-Ethyl-7-ethoxy-4-hydroxy-3-nitrocoumarin
6-n-Propyl-7-ethoxy-4-hydroxy-3-nitrocoumarin
6-Methyl-7-n-propoxy-4-hydroxy-3-nitrocoumarin
6-Ethyl-7-n-propoxy-4-hydroxy-3-nitrocoumarin
6-n-Propyl-7-n-propoxy-4-hydroxy-3-nitrocoumarin Compounds of formula (I) and, of course, formula (IIA) may be prepared by nitrating the parent 4-hydroxycoumarin (II) or (IIA),

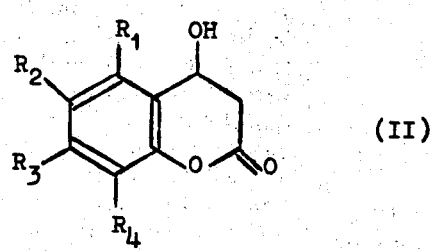

(II)

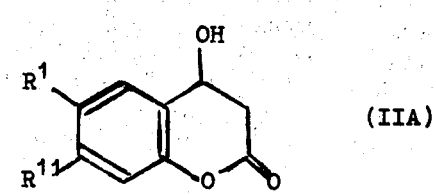

(IIA)

wherein $R_1$, $R_2$, $R_3$ and $R_4$ are as defined in formula (I) and $R^1$ and $R^{11}$ are as defined in formula (IA). Nitration may be effected using one of the following nitrating agents:

i. The nitrous fumes generated with concentrated nitric acid and arsenic oxide.

ii. Acetic acid plus concentrated nitric acid iii. Fuming nitric acid in chloroform iv. Concentrated nitric acid.

Since they are useful intermediates, the present invention includes compounds of formula IIA.

The starting materials of formula (II) may be prepared by any of the standard methods known from the literature for the preparation of 4-hydroxycoumarin. Thus the reaction of the appropriate phenol with malonic acid using phosphorus oxychloride plus zinc chloride as a condensing agent is one possible route.

Using this method 2- or 4- substituted phenols give only one coumarin product but 3- substituted phenols may give a mixture of the two possible isomers. These can usually be separated using standard techniques such as fractional crystallisation. Another method is the condensation of o-hydroxyacetophenones with diethyl carbonate in the presence of sodium or sodium hydride.

The following Examples illustrate the preparation and properties of a number of compounds of formula (I).

EXAMPLE 1

4-Hydroxy-3-nitrocoumarin

Fuming nitric acid (30 ml) was added to a stirred suspension of 4-hydroxycoumarin (5.0g) in chloroform (500 ml) at room temperature over 2 hours. After a further 2 hours, the solvent was removed in vacuo at room temperature and water (250 ml) added to the residue. Filtration gave the product, m.p. 174°, –5°, ($C_9H_5NO_5$ required C, 52.18; H, 2.43; N, 6.76. Found: C, 52.00; H, 2.38; N, 6.62).

EXAMPLE 2

4-Hydroxy-8-methyl-3-nitrocoumarin

Fuming nitric acid (18 ml) was added to a stirred suspension of 4-hydroxy-8-methylcoumarin (m.p. 231°-5°; 3.03g) in chloroform (250 ml) at room temperature over 2 hours. After standing for a further 2 hours, the solvent was removed in vacuo at room temperature and 6N hydrochloric acid (50 ml) added to the residue. Filtration and recrystallisation from ethanol gave the product, m.p. 177°-9°(d), ($C_{10}H_7NO_5$ required C, 54.31; H, 3.19; N, 6.33. Found: C, 54.12; H, 3.35; N, 6.10).

EXAMPLE 3

4-Hydroxy-6methyl-3-nitrocoumarin

Fuming nitric acid (15 ml) was added to a stirred suspension of 4-hydroxy-6-methylcoumarin (m.P. 261°-4°; 2.50g) in chloroform (250 ml) at room temperature over 1.5 hours. After standing for a further 3 hours, the solvent was removed in vacuo at room temperature and water (100 ml) added to the residue. Filtration gave the product, m.p. 171°-171.5°( d). ($C_{10}H_7NO_5$ requires C, 54.31; H, 3.19; N, 6.33. Found: 54.60; H, 3.33; N, 6.60). Recrystallisation from ethanol raised the melting point to 172°-173°(d).

EXAMPLE 4

6-Ethyl-4-hydroxy-3-nitrocoumarin

Fuming nitric acid (33 ml) was added to a stirred suspension of 6-ethyl-4-hydroxycoumarin (m.p. 216°-8°; 5.52g) in chloroform (500 ml) at room temperature over 1 hour. After standing for a further hour, the solvent was removed in vacuo at room temperature and 6N hydrochloric acid (100 ml) added to the residue. Filtration gave the product m.p. 114°-5°, ($C_{11}H_9NO_5$ requires C, 56.17; H, 3.86 N, 5.96. Found: C, 55.86; H, 3.80; N, 5.86). Recrystallisation from benzene-petroleum ether (b.p. 40°-60°) raised the melting point to 117°-9°.

EXAMPLE 5

7,8-Dimethyl-4-hydroxy-3-nitrocoumarin

Fuming nitric acid (26 ml) was added to a stirred suspension of 7,8-dimethyl-4-hydroxycoumarin (m.p. 237-9° (d); 4.42g) in chloroform (400 ml) at room temperature over 1.5 hours. After standing for a further 2 hours, the solvent was removed in vacuo at room temperature and 6N hydrochloric acid (100 ml) added to the residue. Filtration and recrystallisation from ethanol gave the product, m.p. 186°-190° (d), ($C_{11}H_9NO_5$ requires C, 56.18; H, 3.86; N, 5.96. Found: C, 56.38; H, 4.10; N, 5.80).

EXAMPLE 6

6, 8-Dimethyl-4-hydroxy-3-nitrocoumarin

Fuming nitric acid (13 ml) was added to a stirred suspension of 6,8-dimethyl-4-hydroxycoumarin (m.p. 253°– 255°; 2.21g) in chloroform (200 ml) at room temperature over 2 hours. After standing for a further 2 hours, the solvent was removed in vacuo at room temperature and 6N hydrochloric acid (50 ml) added to the residue. Filtration and recrystallisation from ethanol gave the product, m.p. 169.5°-170°(d), ($C_{11}H_9NO_5$ requires C, 56.18; H, 3.86; N, 5.96. Found; C, 56.22; H, 3.99; N, 5.84).

EXAMPLE 7

(i) 6,7-Dimethyl-4-hydroxy-3-nitrocoumarin

Fuming nitric acid (33 ml) was added to a stirred suspension of 6,7-dimethyl-4-hydroxycoumarin (m.p. 252°-3°(d); 5.52g) in chloroform (500 ml) at room temperature over one hour. After standing for a further 2 hours, the solvent was removed in vacuo at room temperature and 6N hydrochloric acid (100 ml) added to the residue. Filtration gave the product, m.p. 200°-201°(d), ($C_{11}H_9NO_5$ requires C, 56.18; H, 3.86; N, 5.96. Found: C, 56.33; H, 4.07; N.5.95). Recrystallisation from ethanol raises the melting point to 203°-4°(d).

(ii) 6,7-Dimethyl-4-hydroxy-3-nitrocoumarin sodium salt

Dilute sodium hydroxide solution was added to a suspension of 6,7-dimethyl-4-hydroxy-3-nitrocoumarin (4.32g) in water (60 ml) till the pH of the solution reached 14. Filtration gave the product, m.p. > 300°, ($C_{11}H_8NO_5Na$ requires C, 51.37; H, 3.14; N, 5.45; Na, 8.94. Found: C, 51.69; H, 3.26; N, 5.33; N, 8.92) after washing briefly with water and drying under vacuum.

EXAMPLE 8

6-Ethyl-4-hydroxy-7-methyl-3-nitrocoumarin

Fuming nitric acid (16 ml) was added to a stirred suspension of 6-ethyl-4-hydroxy-7-methylcoumarin (m.p. 234°–7°; 3.17g) in chloroform (250 ml) at room temperature over 1 hour. After standing for a further hour, the solvent was removed in vacuo at room temperature and 6N hydrochloric acid (60 ml) added to the residue. Filtration gave the product, m.p. 170°–2°(d), ($C_{12}H_{11}NO_5$ requires C, 57.83; H, 4.45; N, 5.62. Found: C, 58.07; H, 4.54; N, 5.76).

EXAMPLE 9

(i) 6,7-Diethyl-4-hydroxy-3-nitrocoumarin

Fuming nitric acid (17 ml) was added to a stirred suspension of 6,7-diethyl-4-hydroxycoumarin (m.p. 213°–6°; 3.46g) in chloroform (300 ml at room temperature over 1.5 hours. After a further hour, the solvent was removed in vacuo at room temperature and 6N hydrochloric acid (70 ml) added to the residue. Filtration gave the product, m.p. 115°–7, ($C_{13}H_{13}NO_5$ requires C, 59.31; H, 4.98; N, 5.32. Found: C, 59.26; H, 5.16; N, 5.25). Recrystallisation from ethanol raised the melting point to 119°–120°.

(ii) 6,7-Diethyl-4-hydroxy-3-nitrocoumarin sodium salt

Dilute sodium hydroxide solution was added to a suspension of 6,7-diethyl-4-hydroxy-3-nitrocoumarin (2.90g) in water (20 ml) till the pH of the solution reached 14. Filtration gave the product as a monohydrate, m.p. 249°–251°(d), ($C_{13}H_{12}NO_5Na.H_2O$ requires C, 51.49; H, 4.65; N, 4.62; Na, 7.58. Found: C, 52.08; H, 4.65; N, 4.83; Na, 7.81) after washing with water and drying under vacuum.

EXAMPLE 10

4-Hydroxy-3-nitro-5,6,7-trimethylcoumarin

Fuming nitric acid (18 ml) was added to a stirred suspension of 4-hydroxy-5,6,7-trimethylcoumarin (m.p. 262°–4°; 3.38g) in chloroform (250 ml) at room temperature over 1.5 hours. After a further 30 minutes, the solvent was removed in vacuo at room temperature and 6N hydrochloric acid (70 ml) added to the residue. Filtration gave the product, m.p. 134°–7°(d), ($C_{12}H_{11}NO_5$ requires C, 57.83; H, 4.45; N, 5.62. Found: C, 57.92; H, 4.57; N, 5.65).

EXAMPLE 11

4,7-Dihydroxy-3-nitrocoumarin

Fuming nitric acid (15 ml) was added to a stirred suspension of 4,7-dihydroxycoumarin monohydrate (m.p. 270°–3°(d); 3.0g) in chloroform (150 ml) at room temperature over 1 hour. After a further 2 hours, the solvent was removed in vacuo at room temperature and 6N hydrochloric acid (50 ml) added to the residue. Filtration and recrystallisation from ethanol gave the product, m.p. 253°–6°(d), ($C_9H_5NO_6$ requires C, 48.44; H. 2.26; N, 6.28. Found: C, 47.78; H, 2.44; N, 6.07).

EXAMPLE 12

4-Hydroxy-7-methoxy-3-nitrocoumarin

Fuming nitric acid (17 ml) was added to a stirred suspension of 4-hydroxy-7-methoxycoumarin (m.p. 258°–260°(d); 3.13g) in chloroform (250 ml) at room temperature over 1.5 hours. After a further 1.5 hours, the solvent was removed in vacuo at room temperature and 6N hydrochloric acid (70 ml) added to the residue. Filtration and recrystallisation from ethanol gave the product, m.p. 167°–8°(d); ($C_{10}H_7NO_6$ requires C, 50.64; H, 2.97; N, 5.91. Found: C, 50.37; H, 3.15; N, 5.60.

EXAMPLE 13

(i) 4-Hydroxy-6-methoxy-3-nitrocoumarin

Fuming nitric acid (30 ml) was added to a stirred suspension of 4-hydroxy-6-methoxycoumarin (m.p. 271°–2°(d); ($C_{10}H_7NO_5$ requires C, 50.64; H, 2.97; N, 5.91. Found: C, 50.78; H, 3.18; N, 5.47).

(ii) 4-Hydroxy-6-methoxy-3-nitrocoumarin sodium salt

Dilute sodium hydroxide solution was added to a suspension of 4-hydroxy-6-methoxy-3-nitrocoumarin (2.0g) in water (40 ml) till the pH of the solution reached 14. Filtration gave the product m.p. 277°–8°(d); ($C_{10}H_6NO_6Na$ requires C, 46.35; H, 2.33; N, 5.41; Na, 8.87. Found: C, 46.32; H, 2.44; N, 5.50; Na, 8.34) after washing briefly with water and drying under vacuum.

EXAMPLE 14

4-Hydroxy-5-methoxy-3-nitrocoumarin

Fuming nitric acid (10 ml) was added to a stirred solution of 4-hydroxy-5-methoxycoumarin (m.p. 154.5°–156°; 1.63g) in chloroform (100 ml) at room temperature over 1 hour. After a further hour, the solvent was removed in vacuo and 6N hydrochloric acid (35 ml) added to the residue. Filtration gave the product, m.p. 175°–177.5°(d), ($C_{10}H_7NO_6$ requires C, 50.64; H, 2.97; N, 5.91. Found: C, 50.54; H, 2.97; N, 5.63).

EXAMPLE 15

7-Ethoxy-4-hydroxy-3-nitrocoumarin

Fuming nitric acid (25 ml) was added to a stirred suspension of 7-ethoxy-4-hydroxycoumarin (m.p. 267°–8°; 5.0g) in chloroform (500 ml) at room temperature over 1.5 hours. After a further two hours, the solvent was removed in vacuo and 6N hydrochloric acid (100 ml) added to the residue. Filtration and recrystallisation from ethanol gave the product, m.p. 153°–4°(d); ($C_{11}H_9NO_6$ requires C, 52.59; H, 3.61; N, 5.58. Found: C, 52.48; H, 3.36; N, 5.29).

EXAMPLE 16

(i) 4-Hydroxy-3-nitro-7-n-propoxycoumarin

Fuming nitric acid (15 ml) was added to a stirred suspension of 4-hydroxy-7-n-propoxycoumarin (m.p. 216°–8°; 3.0g) in chloroform (300 ml) at room temperature over one hour. After a further hour, the solvent was removed in vacuo and 6N hydrochloric acid (60 ml) added to the residue. Filtration and recrystallisation from ethanol gave the product, m.p. 151°–2°, ($C_{12}H_{11}NO_6$ requires C, 54.34; H, 4.18; N, 5.28. Found: C, 54.38; H, 4.28; N, 5.24).

(ii) 4-Hydroxy-3-nitro-7-n-propoxycoumarin sodium salt

Dilute sodium hydroxide solution was added to a suspension of 4-hydroxy-3-nitro-7-n-propoxycoumarin (1.92g) in water (20 ml) till the pH of the solution reached 14. Filtration gave the product, d. at 212°–220°, after washing with water and drying under vacuum.

EXAMPLE 17

6-Benzyloxy-4-hydroxy-3-nitrocoumarin sodium salt

Fuming nitric acid (13 ml) was added to a stirred suspension of 6-benzyloxy-4-hydroxycoumarin (m.p. 226°–8°; 3.13g) in chloroform (200 ml) at room temperature over 1.5 hours. After a further 1.5 hours, the solvent was removed in vacuo at room temperature and water (100 ml) added to the residue. Filtration gave an oily solid which was dissolved in benzene, filtered, and the filtrate evaporated to dryness to give a yellow solid, decomp. 170°. The solid was suspended in water (30 ml) and dilute sodium hydroxide solution added till the pH of the solution reached 14. Filtration gave the product, m.p. 262°–4°(d). ($C_{10}H_{10}NO_6Na$ requires C, 57.32; H, 3.01; N, 4.18; Na, 6.86. Found: C, 57.44; H, 3.31; N, 4.34; Na, 6.86. Found: C, 57.44; H, 3.31; N, 4.34; Na, 6.67) after washing with water and drying under vacuum.

EXAMPLE 18

4-Hydroxy-7-methoxy-8-methyl-3-nitrocoumarin

Fuming nitric acid (15 ml) was added to a suspension of 4-hydroxy-7-methoxy-8-methylcoumarin (m.p. 261°–4°(d); 3.0g) in chloroform (250 ml) at room temperature over one hour. After a further 1.5 hours, the solvent was removed in vacuo at room temperature and 6N hydrochloric acid (60 ml) added to the residue. Filtration and recrystallisation from benzene gave the product, m.p. 195°–7°(d); ($C_{11}H_9NO_6$ requires C, 52.60; H, 3.61; N, 5.58. Found: C, 52.34; H, 3.77; N, 5.65).

EXAMPLE 19

6-Ethyl-4-hydroxy-7-methoxy-3-nitrocoumarin

Fuming nitric acid (15 ml) was added to a suspension of 6-ethyl-4-hydroxy-7-methoxycoumarin (m.p. 262°–5°(d); 2.86g) in chloroform (250 ml) at room temperature over 1 hour. After a further hour, the solvent was removed in vacuo at room temperature and 6N hydrochloric acid (60 ml) added to the residue. Filtration gave the product m.p. 193°–5°(d), ($C_{12}H_{11}NO_6$ requires C, 54.34; H, 4.18; N, 5.28. Found: C, 54.03; H, 4.16; N, 5.21).

EXAMPLE 20

(i) 3,6-Dinitro-4-hydroxycoumarin

4-Hydroxycoumarin (10.0g) was dissolved in concentrated sulphuric acid (20 ml) with stirring and cooling. To this, fuming nitric acid (20 ml) was added over 20 minutes, cooling with ice-water when necessary. After 1 hour, the mixture was poured into ice-water (100 g) and left for 1 hour. Filtration and recrystallisation from benzeneethanol gave the product, m.p. 182°–3°(d), ($C_9H_4N_2O_7$ requires C, 42.87; H, 1.60; N, 11.11. Found: C, 43.24; H, 1.72; N, 10.81).

(ii) 3,6-Dinitro-4-hydroxycoumarin sodium salt

Dilute sodium hydroxide solution was added to a stirred solution of 3,6-dinitro-4-hydroxycoumarin (5.17g) in water (150 ml) till the pH of the solution reached 14. Filtration gave the product, m.p. >310°, ($C_9H_3N_2O_7Na$ requires C, 39.43; H, 1.10; N, 10.22. Found: C, 39.28; H, 1.26; N, 10.17) after washing with water and drying under vacuum.

EXAMPLE 21

(i) 6-Chloro-4-hydroxy-3-nitrocoumarin

Fuming nitric acid (13.5 ml) was added to a stirred suspension of 6-chloro-4-hydroxycoumarin (m.p. 266°–8°; 2.33g) in chloroform (200 ml) at room temperature over 1 hour. After a further two hours, the solvent was removed in vacuo at room temperature and 6N hydrochloric acid (100 ml) added to the residue. Filtration gave the product, m.p. 158°–9°(d), ($C_9H_4NO_5Cl$ requires C, 44.74; H, 1.67; N, 5.80; Cl, 14.68. Found: C, 44.47; H, 1.63; N, 5.72; Cl, 15.02).

(ii) 6-Chloro-4-hydroxy-3-nitrocoumarin sodium salt

Dilute sodium hydroxide solution was added to a stirred suspension of 6-chloro-4-hydroxy-3-nitrocoumarin (2.30g) in water (40 ml) till the pH of the solution reached 14. Filtration gave the product, m.p. >300°, ($C_9H_3NO_5ClNa$ requires C, 41.01; H, 1.15; N, 5.31; Cl, 13.45; Na, 8.72. Found: C, 40.97; H, 1.29; N, 5.34; Cl, 12.68; Na, 8.91) after washing with water and drying under vacuum.

EXAMPLE 22

(i) 7-Chloro-4-hydroxy-3-nitrocoumarin

Fuming nitric acid (27 ml) was added to a stirred suspension of 7-chloro-4-hydroxycoumarin (m.p. 251°–2°, 4.5g) in chloroform (400 ml) at room temperature over 1 hour. After a further 1.5 hours, the solvent was removed in vacuo at room temperature and 6N hydrochloric acid (100 ml) added to the residue. Filtration gave the product, m.p. 174°–5°(d), ($C_9H_4NO_5Cl$ requires C, 44.74; H, 1.67; N, 5.80; Cl, 14.68. Found: C, 44.64; H, 1.81; N, 5.62; Cl, 14.96).

(ii) 7-Chloro-4-hydroxy-3-nitrocoumarin sodium salt

Dilute sodium hydroxide solution was added to a stirred suspension of 7-chloro-4-hydroxy-3-nitrocoumarin (5.1g) in water 60 ml) till the pH of the solution reached 14. Filtration gave the product, d. at 295°, ($C_9H_3NO_5ClNa$ requires C, 41.1; H, 1.15; N, 5.31; Cl, 13.46; Na, 8.72; Found: C, 40.41; H, 1.13; N, 4.90; Cl, 13.64; Na, 9.61) after washing with water and drying under vacuum.

EXAMPLE 23

(i) 6-Bromo-4-hydroxy-3-nitrocoumarin

Fuming nitric acid (17 ml) was added to a stirred suspension of 6-bromo-4-hydroxycoumarin (m.p. 275°–7°; 3.25g) in chloroform (200 ml) at room temperature over 1.5 hours. After a further 2 hours, the solvent was removed in vacuo at room temperature and 6N hydrochloric acid (100 ml) added to the residue. Filtration gave the product, m.p. 161°–4°(d), ($C_9H_4NO_5Br$ requires C, 37.79; H, 1.41; N, 4.90; Br, 27.94. Found: C, 37.86; H, 1.63; N, 5.05; Br, 27.64).

(ii) 6-Bromo-4-hydroxy-3-nitrocoumarin sodium salt

Dilute sodium hydroxide solution was added to a suspension of 6-bromo-4-hydroxy-3-nitrocoumarin (2.80g) in water (20 ml) till the pH of the solution reached 14. Filtration gave the product, m.p. >300°, ($C_9H_3NO_5BrNa$ requires C, 35.09; H, 0.98; N, 4.55; Na, 7.46. Found: C, 35.50; H, 1.16; N, 4.66; Na, 6.98) after washing with water and drying under vacuum.

EXAMPLE 24

(i) 7-Bromo-4-hydroxy-3-nitrocoumarin

Fuming nitric acid (27 ml) was added to a stirred suspension of 7-bromo-4-hydroxycoumarin (m.p. 247.5°–248.5°; 4.18g) in chloroform (400 ml) at room temperature over 1.5 hours. After a further 1.5 hours, the solvent was removed in vacuo at room temperature and 6N hydrochloric acid (100 ml) added to the residue. Filtration gave the product, m.p. 155°–7°, ($C_9H_4NO_5Br$ requires C, 37.79; H, 1.41; N, 4.90; Br, 27.94. Found: C, 37.46; H, 1.45; N, 4.78; Br, 27.93).

(ii) 7-Bromo-4-hydroxy-3-nitrocoumarin sodium salt

Dilute sodium hydroxide solution was added to a suspension of 7-bromo-4-hydroxy-3-nitrocoumarin (4.3 g) in water (50 ml) till the pH of the solution reached 14. Filtration gave the product m.p. 265°–7°(d) after washing with water and drying under vacuum.

EXAMPLE 25

By adding fuming nitric acid to a stirred suspension of 6,7-di-n-propyl-4-hydroxycoumarin in chloroform at room temperature over two hours and following the same general procedure as in Examples 7 and 9, 6,7-di-n-propyl-4-hydroxy-3-nitrocoumarin is formed as the free acid and sodium salt.

By following the same general procedure as in Example 8, but using 6-methyl-7-ethyl-4-hydroxycoumarin as a starting material, 6-methyl-7-ethyl-4-hydroxy-3-nitrocoumarin is obtained.

By following the same general procedure as in Example 19 but using 6-methyl-7-methoxy-4-hydroxycoumarin as a starting material, 6-methyl-7-methoxy-4-hydroxy-3-nitrocoumarin is obtained.

By following the same general procedure as in Example 19 but using 6-n-propyl-7-methoxy-4-hydroxycoumarin as starting material, 6-n-propyl-7-methoxy-4-hydroxy-3-nitrocoumarin is obtained.

By following the same general procedure as in Example 19 but using the following starting materials:

6-methyl-7-ethoxy-4-hydroxycoumarin
6-ethyl-7-ethoxy-4-hydroxycoumarin
6-n-propyl-7-ethoxy-4-hydroxycoumarin
6-methyl-7-n-propoxy-4-hydroxycoumarin
6-ethyl-7-n-propoxy-4-hydroxycoumarin
6-n-propyl-7-n-propoxy-4-hydroxycoumarin
the following compounds are obtained:

6-methyl-7-ethoxy-4-hydroxy-3-nitrocoumarin
6-ethyl-7-ethoxy-4-hydroxy-3-nitrocoumarin
6-n-propyl-7-ethoxy-4-hydroxy-3-nitrocoumarin
6-methyl-7-n-propoxy-4-hydroxy-3-nitrocoumarin
6-ethyl-7-n-propoxy-4-hydroxy-3-nitrocoumarin
6-n-propyl-7-n-propoxy-4-hydroxy-3-nitrocoumarin

EXAMPLE 26

Some of the 4-hydroxycoumarins prepared in the preceding examples were tested in the rat Passive Cutaneous Anaphylaxis Test (PCA test), described below. They were administered as their sodium salts either in pH 7.2 phosphate buffer (for soluble salts) or as a suspension in 1% methyl cellulose (for insoluble salts).

i. Serum containing heat labile homocytotropic antibody was raised in rats by a method similar to that used by Mota. (I. Mota Immunology 1964, 7, 681).

Male Wistar rats of 250–300 g, were injected intraperitoneally with 0.5 ml. of Bordatella pertussis vaccine (containing $4 \times 10^{10}$ dead organism per ml) and subcutaneously with 0.5 ml. of an emulsion of 100 mg. of ovalbumin in 2 ml. of saline and 3 ml. of incomplete Freunds' adjuvant. Rats were bled by cardiac puncture on day 18, the blood was pooled and separated and serum stored at −20° and thawed only once before use.

ii. The P.C.A. test was similar to that described by Ovary and Bier (A. Ovary and O. E. Bier, Prod. Soc. Exp. Biol. Med. 1952, 81, 584) and Goose and Blair (J. Goose and A. M. J. N. Blair, Immunology 1969, 16, 769).

0.1 ml. of each of six twofold serial dilutions of the serum in 0.9% saline were injected intradermally into separate sites on the shaved dorsal surface of 250–350 g. Male Wistar rats. 72 hours later the animals were challenged by i.v. injection of 0.3 ml. of 1% ovalbumin mixed with 0.1 ml. of a 5% solution of pontamine sky blue dye both in isotonic saline buffered with pH. 7.2 Sorenson buffer (P.B.S.). The rats were killed after 20 minutes and the diameter of the blue wheals at the antibody injection sites were measured. The starting dilution of the serum was adjusted so that there was no response, after challenge, at the site of injection of the highest dilution and a maximum response at the two or three lowest dilutions. Typically, six twofold serial dilutions of the serum ¼ to 1/128 were used.

Compounds were tested for their ability to reduce the diameter of the wheals at the injection sites of dilutions of antibody which on all the controls have less than maximum response. Amounts of the compounds were administered to rats by subcutaneous injection, into the nucal region, of a solution of the compound in P.B.S. or as a suspension in 1% methyl cellulose, each amount to a test group of six animals at a specified time prior to intravenous challenge with ovalbumin. The diameters of the blue wheals which developed on the test group of animals were compared with those on a control group of six animals treated in the same way as the test group, but which had received an equivalent subcutaneous injection of the carrier fluid of the same volume but not containing the compound under test.

% Inhibition of P.C.A. = 100 (1 -a/b)

$a$ = The mean of the sum of the diameters of the wheals produced in the test group of animals at those antibody sites where all the control group of animals gave less than maximum response.

$b$ = The mean of the sum of diameters of the wheals produced in the control group of animals at those antibody sites where all the animals in group gave less than maximum response.

The preferred method of administration was a solution of the test compound dissolved in pH 7.2 buffer and neutralised with sodium bicarbonate. For those compounds having insoluble sodium salts, the salts were isolated by reaction of the free nitro compound with 2.5N sodium hydroxide and the filtered sodium salt washed free of alkali with water. The dried salts were then administered as a suspension in 1% methyl cellulose.

Biological Results
| | Dose (mg/kg) | Time (mins) | % Inhibition of PCA response |
|---|---|---|---|
| Example 1. 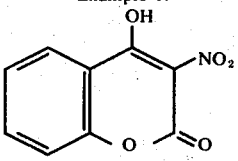 | 2.5 | 0 | 9 |
| | 10 | 0 | 26 |
| | 25 | 0 | 54 |
| | 100 | 0 | 80 |
| | 25 | 30 | 13 |
| | 100 | 30 | 25 |
| Example 2. 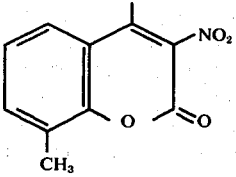 | 25 | 0 | 25 |
| | 100 | 0 | 68 |
| | 25 | 30 | 37 |
| | 100 | 30 | 24 |
| Example 3. 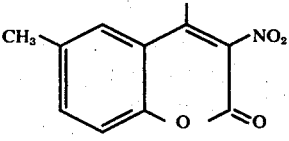 | 25 | 0 | 12 |
| | 100 | 0 | 48 |
| | 25 | 30 | 18 |
| | 100 | 30 | 37 |
| Example 4. 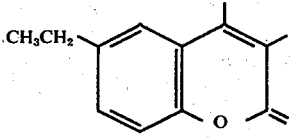 | 25 | 0 | 61 |
| | 100 | 0 | 93 |
| | 25 | 30 | 35 |
| | 100 | 30 | 35 |
| Example 5. 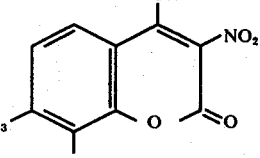 | 25 | 0 | 70 |
| | 100 | 0 | 91 |
| | 25 | 30 | 39 |
| | 100 | 30 | 50 |
| Example 6. 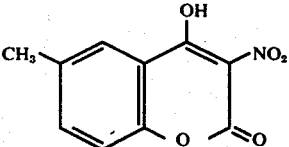 | 25 | 0 | −1 |
| | 100 | 0 | 32 |
| | 25 | 30 | 32 |
| | 100 | 30 | 34 |
| Example 7. 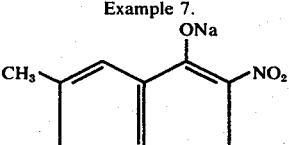 | 25 | 0 | 90 |
| | 100 | 0 | 100 |
| | 25 | 30 | 45 |
| | 100 | 30 | 59 |
| Example 8. 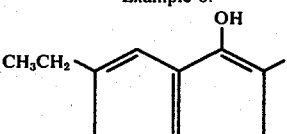 | 25 | 0 | 88 |
| | 100 | 0 | 63 |
| | 25 | 30 | 19 |
| | 100 | 30 | 17 |
| Example 9. 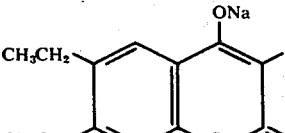 | 25 | 0 | 73 |
| | 100 | 0 | 74 |
| | 25 | 60 | 38 |
| | 100 | 60 | 34 |

-continued

Biological Results

| | Dose (mg/kg) | Time (mins) | % Inhibition of PCA response |
|---|---|---|---|
| Example 10. | 10 | 0 | 22 |
| | 25 | 0 | 58 |
| | 10 | 30 | 37 |
| | 25 | 30 | 29 |
| Example 11. | 25 | 0 | 81 |
| | 80 | 0 | 91 |
| | 25 | 30 | 29 |
| | 80 | 30 | 50 |
| Example 12. | 25 | 0 | 86 |
| | 100 | 0 | 96 |
| | 25 | 30 | 39 |
| | 100 | 30 | 51 |
| Example 13. | 25 | 0 | 35 |
| | 100 | 0 | 45 |
| | 25 | 60 | 11 |
| | 100 | 60 | 40 |
| Example 14. | 25 | 0 | 42 |
| | 100 | 0 | 73 |
| | 25 | 30 | 24 |
| | 100 | 30 | 34 |
| Example 15. | 25 | 0 | 81 |
| | 25 | 30 | 41 |
| Example 16. | 25 | 0 | 82 |
| | 25 | 30 | 36 |
| Example 17. | 25 | 0 | −1 |
| | 100 | 0 | 8 |
| | 25 | 60 | 19 |
| | 100 | 60 | 22 |
| Example 18. | 25 | 0 | 78 |
| | 100 | 0 | 57 |
| | 25 | 30 | 32 |
| | 100 | 30 | 38 |

-continued

Biological Results

| | Dose (mg/kg) | Time (mins) | % Inhibition of PCA response |
|---|---|---|---|
| Example 19. | 25 | 0 | 47 |
| | 100 | 0 | 76 |
| | 25 | 30 | 38 |
| | 50 | 30 | 31 |
| Example 20. | 25 | 0 | 13 |
| | 100 | 0 | 18 |
| | 25 | 60 | 58 |
| | 100 | 60 | 55 |
| Example 21. | 25 | 0 | −3 |
| | 100 | 0 | 11 |
| | 25 | 60 | 36 |
| | 100 | 60 | 54 |
| Example 22. | 25 | 0 | 12 |
| | 100 | 0 | 13 |
| | 25 | 60 | 17 |
| | 100 | 60 | 39 |
| Example 23. | 25 | 0 | −30 |
| | 100 | 0 | −14 |
| | 25 | 60 | 34 |
| | 100 | 60 | 40 |
| Example 24. | 25 | 0 | 9 |
| | 100 | 0 | 54 |
| | 25 | 60 | 21 |
| | 100 | 60 | 28 |

We claim:
1. A pharmaceutical composition in a form suitable for oral, parenteral or insufflation administration to humans which comprises a compound of the formula (I)

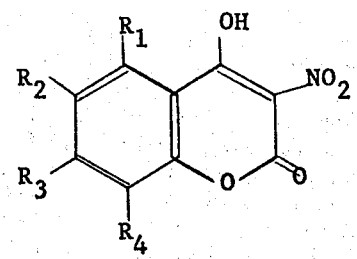

or a pharmaceutically acceptable non-toxic salt thereof, wherein $R_1$, $R_2$, $R_3$ and $R_4$ are each hydrogen, alkyl of 1 to 4 carbon atoms, alkoxy of 1 to 4 carbon atoms, phenoxy, benzyloxy, phenyl, benzyl, pyridyl, hydroxy, nitro, or halogen or any two of the groups $R_1$, $R_2$, $R_3$ and $R_4$ taken together with the carbon atoms to which they are joined form a phenyl or 1,2-cyclohexenylene ring, in an amount sufficient to be effective for the prophylaxis of asthma, hayfever, or rhinitis in combination with a pharmaceutically acceptable non-toxic inert diluent or carrier suitable for said administration form.

2. A pharmaceutical composition according to claim 1 wherein the compound is of the formula (IA):

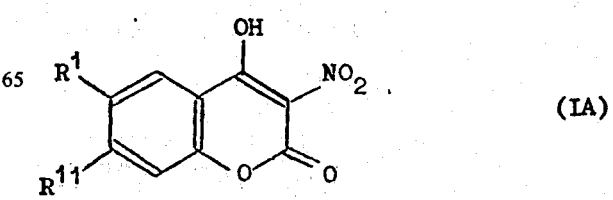

or a pharmaceutically acceptable non-toxic salt thereof, wherein $R^1$ is hydrogen, methyl, ethyl, n-propyl, methoxy, ethoxy, n-propoxy and $R^{11}$ is methyl, ethyl, n-propyl, methoxy, ethoxy or n-propoxy.

3. A pharmaceutical composition according to claim 2 wherein the compound is 6,7-dimethyl-4-hydroxy-3-nitrocoumarin or a pharmaceutically acceptable non-toxic salt thereof.

4. A pharmaceutical composition according to claim 1 wherein the compound is in the form of the salt.

5. A pharmaceutical composition according to claim 4 wherein the salt is the sodium salt.

6. A pharmaceutical composition according to claim 1 in the form of a microfine powder for insufflation.

7. A pharmaceutical composition according to claim 6 which additionally contains a small amount of a bronchodilator.

8. A pharmaceutical composition according to claim 7 wherein the bronchodilator is isoprenaline.

9. A pharmaceutical composition according to claim 1 in which the diluent or carrier is a sterile liquid suitable for injection.

10. A pharmaceutical composition according to claim 1 in the form of a pill, a tablet or a capsule, or a powder which is suitable for mixing with water to form a syrup.

11. A pharmaceutical composition according to claim 1 wherein $R_1$ and $R_4$ are each hydrogen and $R_2$ and $R_3$ are each methyl, ethyl, propyl, methoxy, ethoxy or propoxy.

12. A pharmaceutical composition according to claim 1 wherein $R_1$, $R_2$, $R_3$ and $R_4$ are each hydrogen, methyl, ethyl, propyl, methoxy, ethoxy, propoxy, benzyloxy, hydroxy, nitro, chloro or bromo.

13. A pharmaceutical composition according to claim 1 wherein the compound is in the form of an alkali metal salt, an alkaline earth metal salt, an amine salt or an amino salt.

14. A pharmaceutical composition according to claim 2 wherein the compound is 6,7-diethyl-4-hydroxy-3-nitrocoumarin or a pharmaceutically acceptable non-toxic salt thereof.

15. A pharmaceutical composition according to claim 2 wherein the compound is 6,7-di-n-propyl-4-hydroxy-3-nitrocoumarin or a pharmaceutically acceptable non-toxic salt thereof.

16. A pharmaceutical composition according to claim 2 wherein the compound is 6-methyl-7-ethyl-4-hydroxy-3-nitrocoumarin or a pharmaceutically acceptable non-toxic salt thereof.

17. A pharmaceutical composition according to claim 2 wherein the compound is 6-ethyl-7-methyl-4-hydroxy-3-nitrocoumarin or a pharmaceutically acceptable non-toxic salt thereof.

18. A pharmaceutical composition according to claim 2 wherein the compound is 7-methoxy-4-hydroxy-3-nitrocoumarin or a pharmaceutically acceptable non-toxic salt thereof.

19. A pharmaceutical composition according to claim 2 wherein the compound is 7-ethoxy-4-hydroxy-3-nitrocoumarin or a pharmaceutically acceptable non-toxic salt thereof.

20. A pharmaceutical composition according to claim 2 wherein the compound is 7-n-propoxy-4-hydroxy-3-nitrocoumarin or a pharmaceutically acceptable non-toxic salt thereof.

21. A pharmaceutical composition according to claim 2 wherein the compound is 6-methyl-7-methoxy-4-hydroxy-3-nitrocoumarin or a pharmaceutically acceptable non-toxic salt thereof.

22. A pharmaceutical composition according to claim 2 wherein the compound is 6-ethyl-7-methoxy-4-hydroxy-3-nitrocoumarin, or a pharmaceutically acceptable non-toxic salt thereof.

23. A pharmaceutical composition according to claim 2 wherein the compound is 6-n-propyl-7-methoxy-4-hydroxy-3-nitrocoumarin or a pharmaceutically acceptable non-toxic salt thereof.

24. A pharmaceutical composition according to claim 2 wherein the compound is 6-methyl-7-ethoxy-4-hydroxy-3-nitrocoumarin, or a pharmaceutically acceptable non-toxic salt thereof.

25. A pharmaceutical composition according to claim 2 wherein the compound is 6-ethyl-7-ethoxy-4-hydroxy-3-nitrocoumarin or a pharmaceutically acceptable non-toxic salt thereof.

26. A pharmaceutical composition according to claim 2 wherein the compound is 6-n-propyl-7-ethoxy-4-hydroxy-3-nitrocoumarin or a pharmaceutically acceptable non-toxic salt thereof.

27. A pharmaceutical composition according to claim 2 wherein the compound is 6-methyl-7-n-propoxy-4-hydroxy-3-nitrocoumarin or a pharmaceutically acceptable non-toxic salt thereof.

28. A pharmaceutical composition according to claim 2 wherein the compound is 6-ethyl-7-n-propoxy-4-hydroxy-3-nitrocoumarin or a pharmaceutically acceptable non-toxic salt thereof.

29. A pharmaceutical composition according to claim 2 wherein the compound is 6-n-propyl-7-n-propoxy-4-hydroxy-3-nitrocoumarin or a pharmaceutically acceptable non-toxic salt thereof.

30. A method for the prophylaxis of asthma, hayfever and rhinitis in humans which comprises administering to a human in need thereof orally, parenterally or by insufflation a compound of the formula (I)

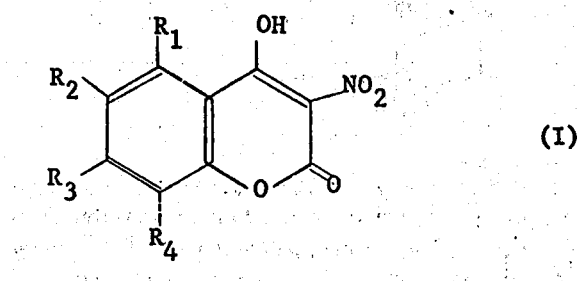

(I)

or a pharmaceutically acceptable non-toxic salt thereof, wherein $R_1$, $R_2$, $R_3$ and $R_4$ are each hydrogen, alkyl of 1 to 4 carbon atoms, alkoxy of 1 to 4 carbon atoms, phenoxy, benzyloxy, phenyl, benzyl, pyridyl, hydroxy, nitro, or halogen or any two of the groups $R_1$, $R_2$, $R_3$ and $R_4$ taken together with the carbon atoms to which they are joined form a phenyl or 1,2-cyclohexenylene ring, in an amount sufficient to be effective for the prophylaxis of asthma, hayfever or rhinitis, in combination with a pharmaceutically acceptable non-toxic inert diluent or carrier suitable for said administration form.

31. A method according to claim 30 wherein the compound is of the formula (IA):

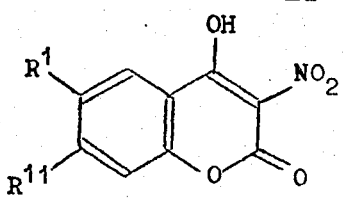

(IA)

or a pharmaceutically acceptable non-toxic salt thereof, wherein $R^1$ is hydrogen, methyl, ethyl, n-propyl, methoxy, ethoxy, n-propoxy and $R^{11}$ is methyl, ethyl, n-propyl, methoxy, ethoxy or n-propoxy.

32. A method according to claim 30 wherein $R_1$ and $R_4$ are each hydrogen and $R_2$ and $R_3$ are each methyl, ethyl, propyl, methoxy, ethoxy or propoxy.

33. A method according to claim 30 wherein $R_1$, $R_2$, $R_3$ and $R_4$ are each hydrogen, methyl, ethyl, propyl, methoxy, ethoxy, propoxy, benzyloxy, hydroxy, nitro, chloro or bromo.

34. A method according to claim 30 wherein the compound is in the form of an alkali metal salt, an alkaline earth metal salt, an amine salt or an amino salt.

35. A method according to claim 30 wherein the compound is in the form of the salt.

36. A method according to claim 35 wherein the salt is the sodium salt.

37. A method according to claim 30 wherein the compound is 6,7-dimethyl-4-hydroxy-3-nitrocoumarin or a pharmaceutically acceptable non-toxic salt thereof.

38. A method according to claim 30 wherein the compound is 6,7-diethyl-4-hydroxy-3-nitrocoumarin or a pharmaceutically acceptable non-toxic salt thereof.

39. A method according to claim 30 wherein the compound is 6,7-di-n-propyl-4-hydroxy-3-nitrocoumarin or a pharmaceutically acceptable non-toxic salt thereof.

40. A method according to claim 30 wherein the compound is 6-methyl-7-ethyl-4-hydroxy-3-nitrocoumarin or a pharmaceutically acceptable non-toxic salt thereof.

41. A method according to claim 30 wherein the compound is 6-ethyl-7-methyl-4-hydroxy-3-nitrocoumarin or a pharmaceutically acceptable non-toxic salt thereof.

42. A method according to claim 30 wherein the compound is 7-methoxy-4-hydroxy-3-nitrocoumarin or a pharmaceutically acceptable non-toxic salt thereof.

43. A method according to claim 30 wherein the compound is 7-ethoxy-4-hydroxy-3-nitrocoumarin or a pharmaceutically acceptable non-toxic salt thereof.

44. A method according to claim 30 wherein the compound is 7-n-propoxy-4-hydroxy-3-nitrocoumarin or a pharmaceutically acceptable non-toxic salt thereof.

45. A method according to claim 30 wherein the compound is 6-methyl-7-methoxy-4-hydroxy-3-nitrocoumarin or a pharmaceutically acceptable non-toxic salt thereof.

46. A method according to claim 30 wherein the compound is 6-ethyl-7-methoxy-4-hydroxy-3-nitrocoumarin or a pharmaceutically acceptable non-toxic salt thereof.

47. A method according to claim 30 wherein the compound is 6-n-propyl-7-methoxy-4-hydroxy-3-nitrocoumarin or a pharmaceutically acceptable non-toxic salt thereof.

48. A method according to claim 30 wherein the compound is 6-methyl-7-ethoxy-4-hydroxy-3-nitrocoumarin or a pharmaceutically acceptable non-toxic salt thereof.

49. A method according to claim 30 wherein the compound is 6-ethyl-7-ethoxy-4-hydroxy-3-nitrocoumarin or a pharmaceutically acceptable non-toxic salt thereof.

50. A method according to claim 30 wherein the compound is 6-n-propyl-7-ethoxy-4-hydroxy-3-nitrocoumarin or a pharmaceutically acceptable non-toxic salt thereof.

51. A method according to claim 30 wherein the compound is 6-methyl-7-n-propoxy-4-hydroxy-3-nitrocoumarin or a pharmaceutically acceptable non-toxic salt thereof.

52. A method according to claim 30 wherein the compound is 6-ethyl-7-n-propoxy-4-hydroxy-3-nitrocoumarin or a pharmaceutically acceptable non-toxic salt thereof.

53. A method according to claim 30 wherein the compound is 6-n-propyl-7-n-propoxy-4-hydroxy-3-nitrocoumarin or a pharmaceutically acceptable non-toxic salt thereof.

54. A method according to claim 30 wherein the compound and the diluent or carrier are in the form of a microfine powder and the administration is by insufflation.

55. A method according to claim 54 wherein the compound and the diluent or carrier additionally contain a small amount of a bronchodilator.

56. A method according to claim 55 wherein the bronchodilator is isoprenaline.

57. A method according to claim 30 wherein the diluent or carrier is a sterile liquid suitable for injection and the administration is by injection.

58. A method according to claim 30 wherein the compound and the diluent or carrier are in the form of a pill, a tablet, or a capsule, or a powder which is suitable for mixing with water to form a syrup and the administration is oral.

* * * * *